United States Patent
Selner

(10) Patent No.: US 11,318,035 B2
(45) Date of Patent: May 3, 2022

(54) INSTRUMENTED ORTHOTIC

(71) Applicant: Allen Joseph Selner, Manhattan Beach, CA (US)

(72) Inventor: Allen Joseph Selner, Manhattan Beach, CA (US)

(*) Notice: Subject to any disclaimer, the term of this patent is extended or adjusted under 35 U.S.C. 154(b) by 172 days.

(21) Appl. No.: 15/583,973

(22) Filed: May 1, 2017

(65) Prior Publication Data

US 2017/0319368 A1    Nov. 9, 2017

Related U.S. Application Data

(63) Continuation of application No. PCT/US2017/030303, filed on Apr. 29, 2017.
(Continued)

(51) Int. Cl.
    *A61F 5/01*      (2006.01)
    *A61B 5/11*      (2006.01)
    (Continued)

(52) U.S. Cl.
    CPC .............. *A61F 5/0127* (2013.01); *A43B 3/34* (2022.01); *A43B 17/00* (2013.01); *A61B 5/0004* (2013.01);
    (Continued)

(58) Field of Classification Search
    None
    See application file for complete search history.

(56) References Cited

U.S. PATENT DOCUMENTS

| 6,195,921 B1* | 3/2001 | Truong | A43B 3/00 340/573.1 |
| 2003/0009308 A1* | 1/2003 | Kirtley | A61B 5/1038 702/141 |

(Continued)

FOREIGN PATENT DOCUMENTS

| CN | 104257393 A | 1/2015 |
| WO | 2015/069781 A1 | 5/2015 |

OTHER PUBLICATIONS

Crea et al. A Wireless Flexible Sensorized Insole for Gait Analysis; 2014; Sensors 2014, 14, 1073-1093; (Year: 2014).*
(Continued)

*Primary Examiner* — Jay B Shah
(74) *Attorney, Agent, or Firm* — Pillsbury Winthrop Shaw Pittman LLP

(57) ABSTRACT

A semi-rigid foot orthotic can have 3-axis accelerometers, gyroscopes, magnetometers, and strain gauges embedded in one or more flexible regions along with a microprocessor and wireless transmitter. Data from the sensors can be used to track the gait cycle. Data on the flexing, bending, or rotating of portions of the orthotic are processed and compared to ideal or data from other runs to rate the effectiveness of the orthotic. The orthotic and the sole of the shoe have relative freedom of motion between them. By doing a 3D comparing of the location, motion and orientation of the shoe from the same information for at least one orthotic region; determining shoe-to-orthotic relative motion. Modifications or adjustments can be made to improve the user-experience. The computation can involve either or both of a cloud based server and an external hand-held device in wireless communication with the orthotic.

28 Claims, 9 Drawing Sheets

Related U.S. Application Data

(60) Provisional application No. 62/331,915, filed on May 4, 2016.

(51) Int. Cl.
    *A61B 5/00*       (2006.01)
    *A61B 5/103*     (2006.01)
    *A43B 3/34*      (2022.01)
    *A43B 17/00*     (2006.01)

(52) U.S. Cl.
CPC ............ *A61B 5/1038* (2013.01); *A61B 5/112* (2013.01); *A61B 5/4836* (2013.01); *A61B 5/4848* (2013.01); *A61B 5/6807* (2013.01); *A61B 5/72* (2013.01); *A61B 5/742* (2013.01); *A61B 5/0022* (2013.01); *A61B 2560/0475* (2013.01); *A61B 2562/0219* (2013.01); *A61B 2562/0247* (2013.01)

(56) References Cited

U.S. PATENT DOCUMENTS

| | | |
|---|---|---|
| 2006/0135883 A1* | 6/2006 | Jonsson ................ A61F 2/6607 600/546 |
| 2008/0287832 A1 | 11/2008 | Collins et al. |
| 2008/0306410 A1 | 12/2008 | Kalpaxis et al. |
| 2010/0324455 A1 | 12/2010 | Rangel et al. |
| 2011/0214501 A1 | 9/2011 | Ross et al. |
| 2012/0143092 A1 | 6/2012 | Xia |
| 2012/0253234 A1 | 10/2012 | Yang et al. |
| 2013/0219745 A1 | 8/2013 | Moreno-Collado |
| 2013/0324887 A1 | 12/2013 | Pas et al. |
| 2015/0100105 A1 | 4/2015 | Kiani et al. |
| 2015/0257679 A1 | 9/2015 | Ross |
| 2016/0066818 A1 | 3/2016 | Cowley et al. |
| 2016/0249829 A1* | 9/2016 | Trabia ................ A61B 5/112 600/592 |

OTHER PUBLICATIONS

PCT International Search Report KIPO PCT/US2017/030303 filed Apr. 29, 2017.

China National Intellectual Property Administration, Chinese Office Action issued in Chinese Application No. 2017800358954, dated Sep. 2, 2020, pp. 1-11.

European Patent Office, Official Action issued in EP Patent Application No. 17793054.2, dated Mar. 17, 2021, pp. 1-8.

Bamberg et al., "Gait Analysis Using a Shoe-Integrated Wireless Sensor System", IEEE Transactions on Information Technology in Biomedicine, Jul. 1, 2008, pp. 413-423, vol. 12(4).

Patent Cooperation Treaty, "International Preliminary Report on Patentability and Written Opinion of the International Searching Authority", re application PCT/US2017/030303 of applicant Selner, Allen Joseph dated Nov. 15, 2018, 8 pages.

\* cited by examiner

401

INSTRUMENTED ORTHOTIC

RELATED APPLICATIONS

This application hereby claims the benefit of, and incorporates in its entirety U.S. provisional application 62/331,915, filed May 4, 2016, by reference herein. The present application is a continuation of application PCT/US17/30303 filed Apr. 29, 2017; that also claims the benefit of U.S. provisional application 62/331,915.

FIELD

This disclosure is related to a device and method for data collection and analysis of dynamic orthotic performance.

BACKGROUND

Optimum fitting of foot orthotics to a particular user can be thought of as much an art as a science. It is said that some people are helped enormously even by a rolled up piece of newspaper put in their shoe, while others require multiple visits to a podiatrist for fine-tuning, usually accomplished by adding or removing material from an orthotic. For many years the prevailing thought that "supporting the arch" was the best way to control gait but newer thinking has focused on designing orthotics to restrict and influence motion as well as improve dynamic alignment of the joints in the lower extremity.

This improved alignment reduces the rotational and vertical joint forces resulting from ground reaction forces being transmitted up the kinetic chain of the lower extremity. To restrict and influence motion, newer orthotics are constructed from semi-rigid materials that flex, bend, or rotate under load. During the stance phase of the gait cycle (from heel strike, through mid-stance, to propulsion) weight is placed on the orthotic causing a complex flexing, bending, or rotating in three planes—the sagittal, frontal, and transverse, at multiple regions on the orthotic. All of that movement occurs in the shoe, under the foot and thus is not information directly available to a clinician evaluating the effectiveness of the orthotic. Although a clinician can carefully watch a person walking back and forth while wearing a trial orthotic, the users' reported subjective experience provides the primary clues to the clinician. That often is not any more helpful than "it doesn't feel right".

It is desirable to make fitting an orthotic to an individual more science and less art. It is also desirable to reduce the need for a clinician in many cases and to lower the overall cost of getting effective orthotics on users' feet.

SUMMARY

The problem is solved by an instrumented, semi-rigid orthotic. One or more flexible portions of the orthotic can have embedded or secured sensors to detect and measure flexing, bending, or rotating in three planes. The sensors can include accelerometers, gyroscopes, magnetometers, strain gauges, and force transducers at one or more locations on the orthotic. Data can be read from those sensors by a microprocessor that also can be embedded in or secured to the orthotic. Preprocessing of the data can be performed by the microprocessor and further processing can be optionally performed on an external computing device like a smart phone or tablet computer or cloud-based server. The external device can be in wired or wireless communication with the microprocessor. Results can be displayed on the portable device.

Preprocessing of the raw data can include determining the direction, magnitude and timing of flexing, bending, or rotating of the orthotic leading to data about the motions of the subtalar and midtarsal joints. Preprocessing can also extract the duration, position, velocity and acceleration of any flexing, bending, or rotating at multiple locations on the orthotic. The timing can be meaningfully expressed in terms of the point in the stance phase of a gait cycle that an event occurs. This allows measurement and recording of the bending and the motion at the same time. Comparison to data previously taken from that subject or other subjects with the same or other orthotics can be made to determine the effectiveness of the orthotic. Orthotic effectiveness is more than the user's subjective experience; it can also include achieving an optimal clinical alignment of the entire lower extremity. Further, recommendations for altering the geometry or rigidity of the orthotic can be a component of the results produced by the analysis. If the orthotic was one with variable tilt settings, the recommendation to alter the geometry could be recommending a new setting. Measuring how the foot and also the thigh move can help create an algorithm to use orthotic flexing, bending, or rotating to evaluate issues with foot, knee and ankle motion.

Each movement pattern the sensors pick up during walking, swinging a golf club, a cycling stroke, or during any other movement tasks represent distinct patterns that can be grouped into categories, studied, and used in a model. With adjustable orthotics, gait patterns can be modified. Some applications will combine data from an instrumented orthotic with more traditional measurements of ground reaction forces or motion capture.

This is important because the ground reaction forces are transmitted up the entire lower extremity, often resulting in excessive loads and strains on the bones and joints of the lower extremity. These excessive loads on mal-alignment of the joints of the lower extremity can lead to injuries and poor performance in sports and other functional tasks.

The use of the data analytics can create a database used to structurally classify and develop motion metrics for different structural variations of the lower extremity.

DETAILED DESCRIPTION

System

Figure 1:
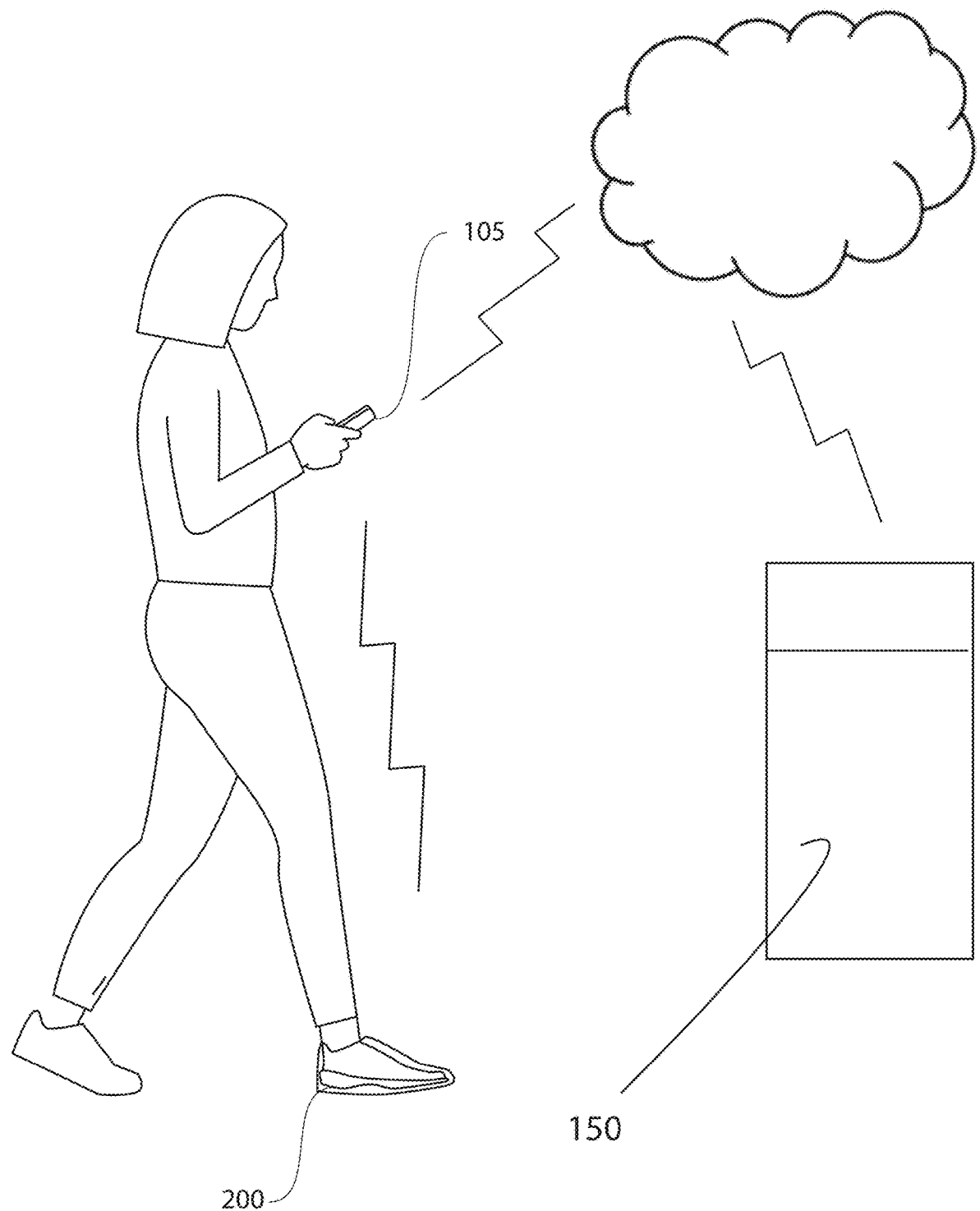
FIG. 1 shows a schematic representation of a system for capturing orthotic performance in use.

In FIG. 1 a user is shown examining, on her smart phone 105, the rating produced by the instrumented orthotic system 200 she is wearing.

Figure 2:
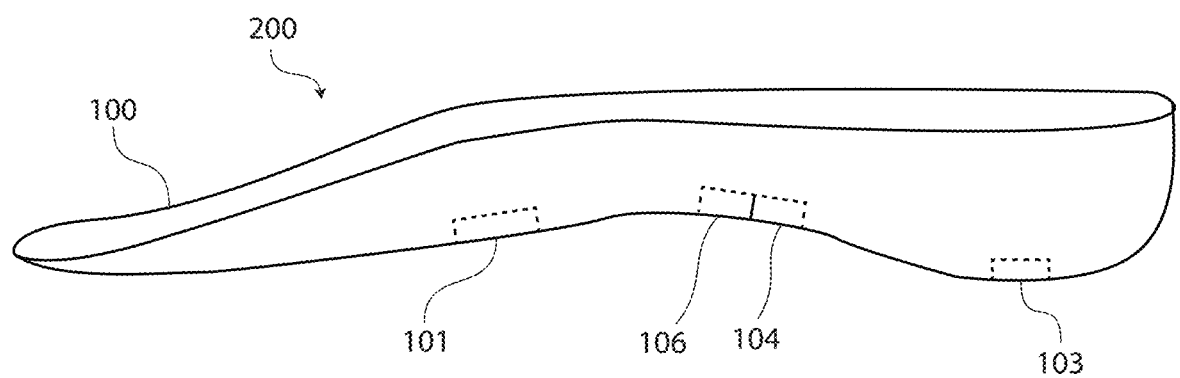
FIG. 2 shows, in schematic form, an instrumented orthotic plate with embedded sensors and computing components in dashed lines.

FIG. 2 shows the positions of sensors and computing and communicating devices in an example embodiment of an instrumented orthotic. There are position, movement, and orientation sensors in a flexible forefoot area 101 and near the arch 106. In addition, this embodiment includes a pressure or force sensor 103 at the heel. These devices are electrically connected to a computing unit or microprocessor 104. The sensors and CPU are thin enough to be embedded in the orthotic and not interfere with its function.

Figure 3:
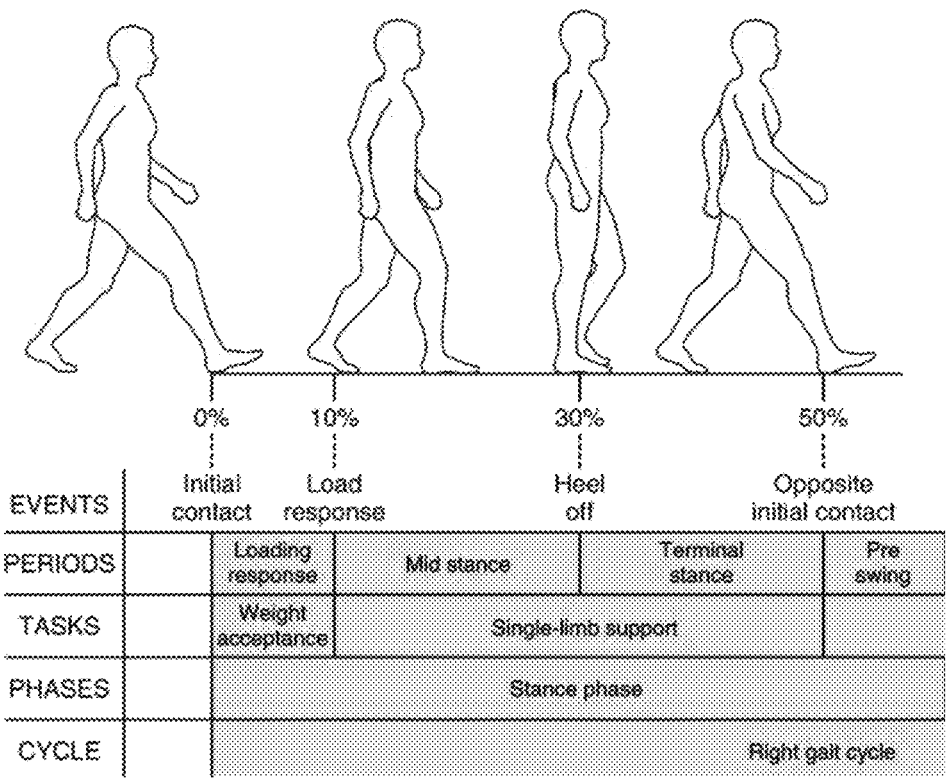
FIG. 3 Illustrates points in the stance phase of a gait cycle.

FIG. 3 illustrates points of the gait cycle during the stance phase. The stance phase is from heel strike to toe propulsion. This is the phase in which the most useful data is obtained by the system since the orthotic is under load.

Figure 4:
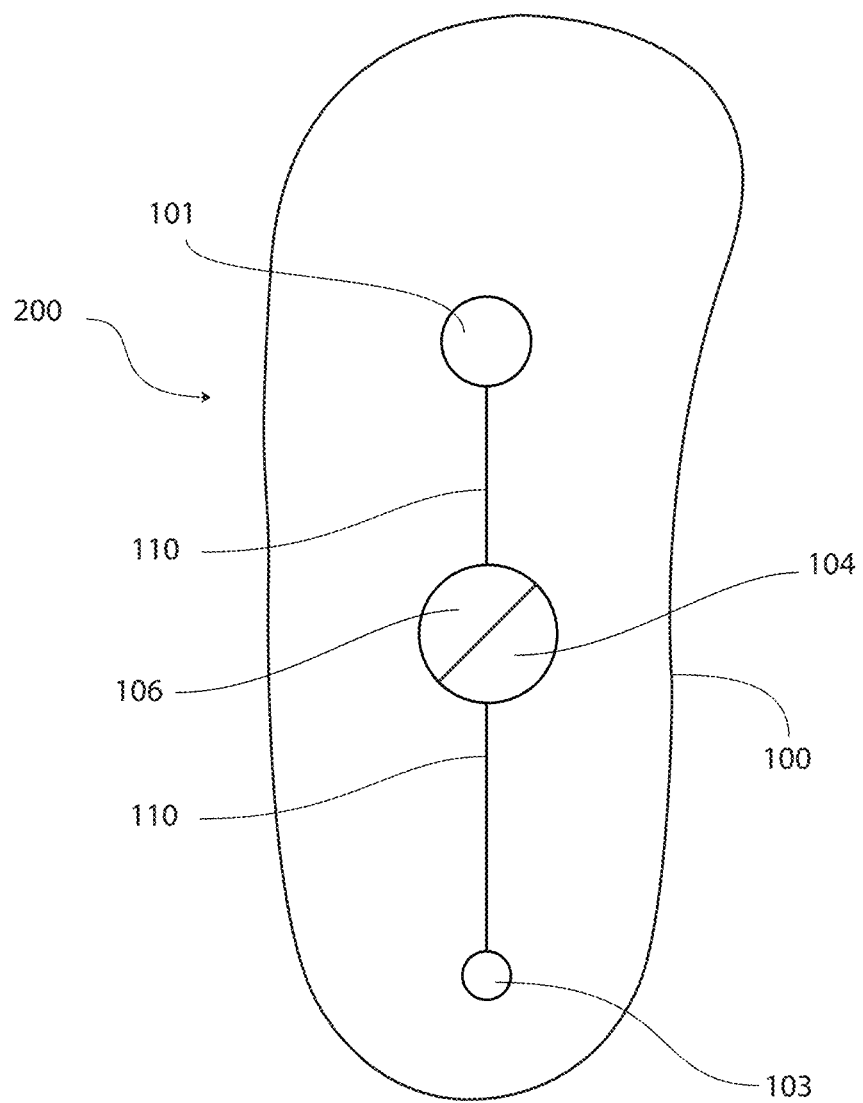
FIG. 4 shows the underside of the device of FIG. 2 in a schematic representation of the locations of sensors, CPU and electronic interconnect between the electronic components.
Figure 5A:
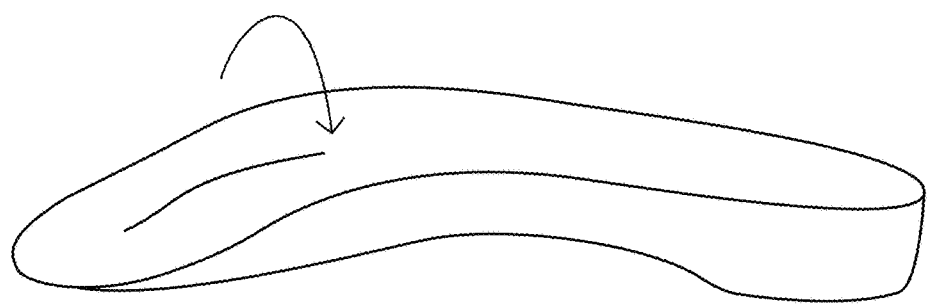
FIGS. 5a-5d show exaggerated states of flexing, bending, or rotating of a flexible forefoot region of the device of FIG. 2.
Figure 5B:
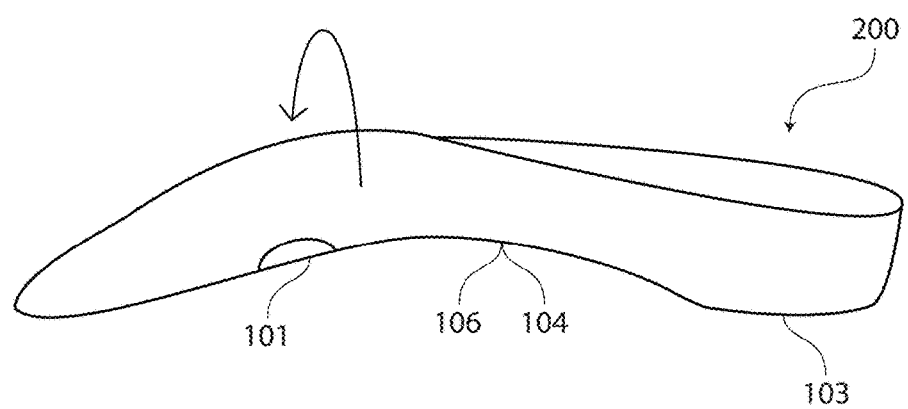
Figure 5C:
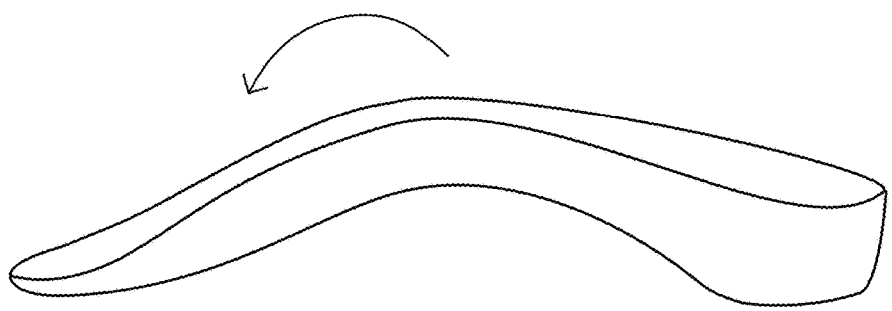
Figure 5D:
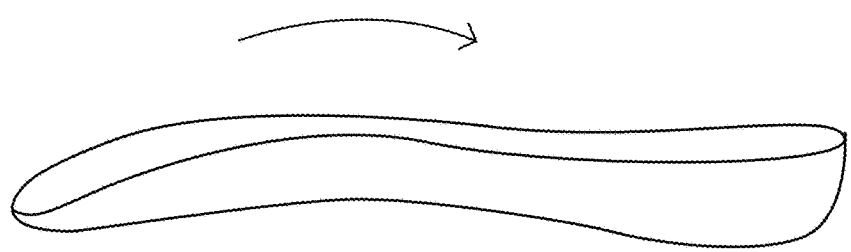

FIG. 4 shows a schematic representation of the instrumented orthotic of FIG. 1. The electrical interconnection 110 is depicted in this figure.

In a much exaggerated way, FIGS. 5a-5d show possible flexing, bending, or rotating of the forefoot region. In attempting to control for over-pronation or over-supination, the forefoot orthotic will flex, bend, or rotate during points in the gait cycle when weight is put on the forefoot. This flexing, bending, or rotating will typically be a complex motion in three dimensions. If known, the direction and degree of flexing, bending, or rotating can inform a clinician who is trying to achieve an optimal clinical alignment of the lower extremity.

Figure 6:
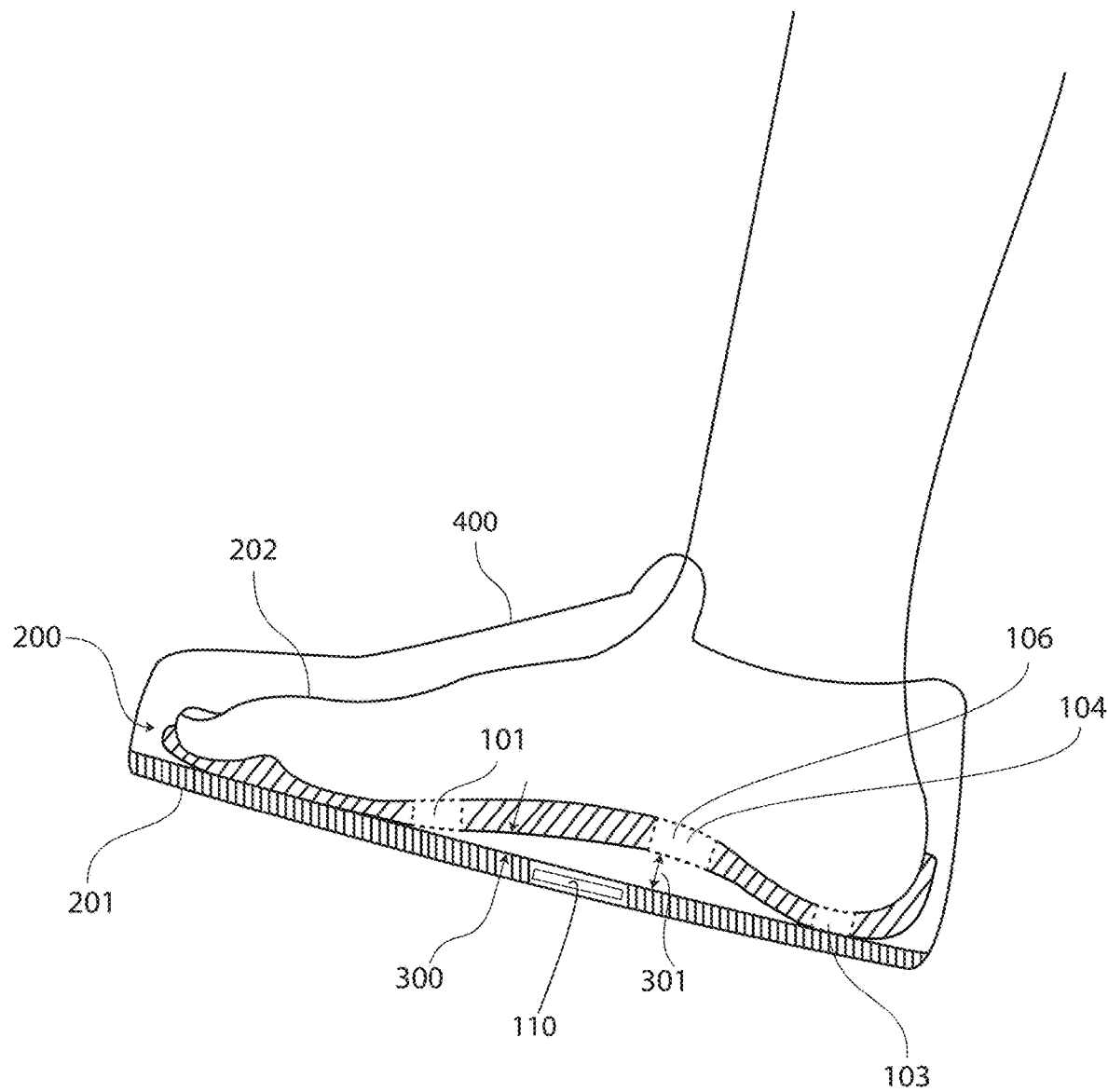
FIG. 6 is a simplified cut-away view of a foot in a shoe with an instrumented orthotic.

FIG. 6 shows a cut-away schematic view of an instrumented orthotic 200 of these teachings. It is shown being worn within a shoe 400 and supporting a foot 202. While the portions of the orthotic under the toes and heel rest directly on the sole of the shoe when weight is fully applied, the orthotic can also move in relation to the sole of the shoe at various points in the gait cycle. Regions 300 and 301 have three-dimensional freedom of movement with respect to the sole 201 of the shoe, and ultimately to the ground. These motions can be sensed by the two sets of sensors 101, 106 in this embodiment. Some alternative embodiments have a wireless sensor 110 in the shoe.

Figure 7:
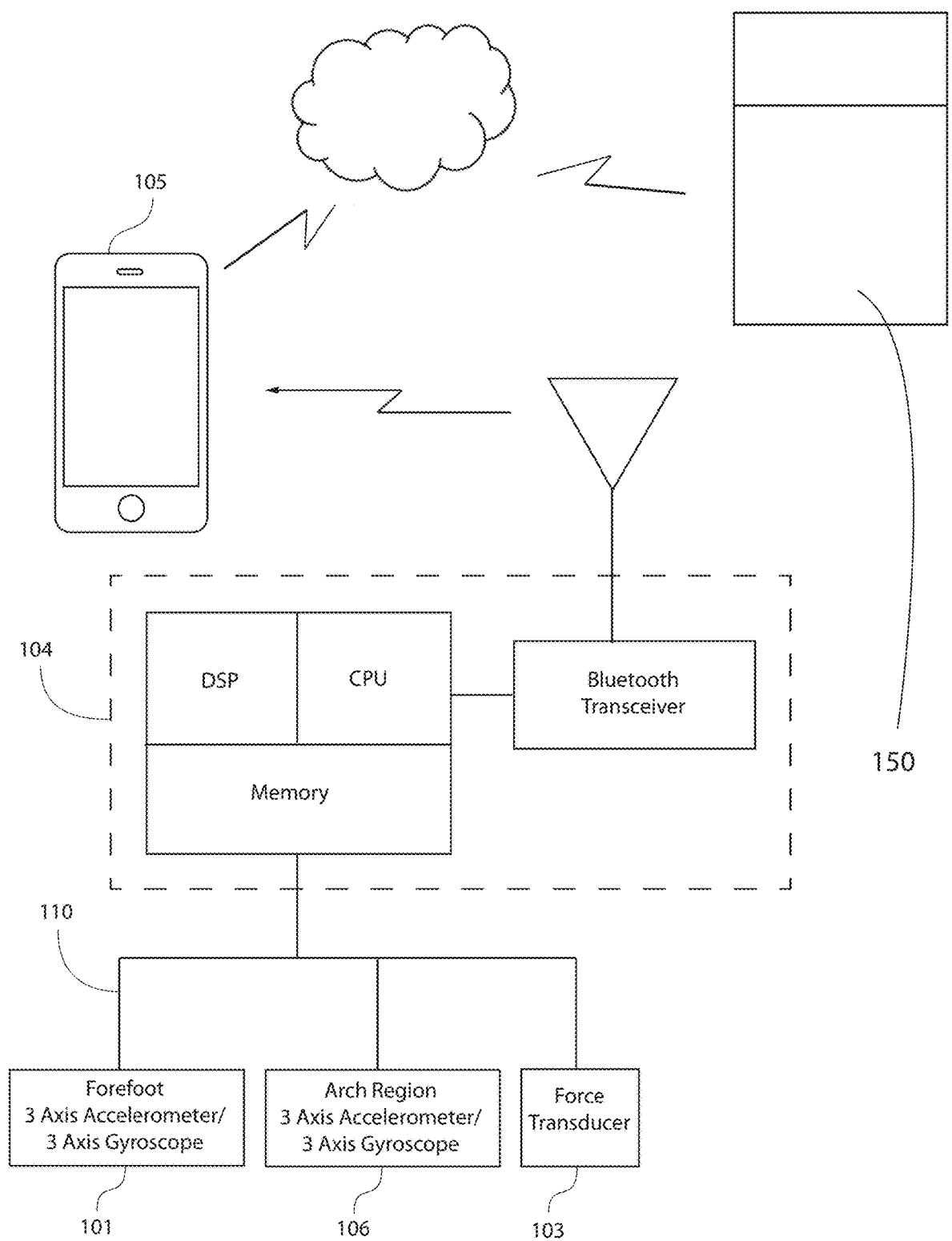
FIG. 7 shows a simplified block diagram of the electronics in the system of FIG. 4 including the portion embedded in the orthotic plate and a portion in an external computing device.

FIG. 7 shows a block diagram of the electronics subsystem. The sensors are connected to an integrated circuit that has a processor, memory, and communication abilities. In this example, an integrated digital signal processor (DSP) is included in the example CPU.

An electronic system, according to this block diagram, includes a microprocessor 104, a forefoot 3-axis accelerometer/3-axis gyroscope 101, an arch region 3-axis accelerometer/3-axis gyroscope 106, and a wireless transmitter 111. The components are embedded in the orthotic. Suitable components can include the Intel® Quark™ SE microcontroller, said to be the heart of the Intel Curie. The Quark™ SE CPU would be connected to a 3-axis accelerometer, and 3-axis gyroscope, and 3-axis magnetometer IC, also embedded in the orthotic. The STMicroelectronics LSM9DS0 9DOF IMU IC would be a suitable component for this purpose. Strain gauges in two dimensions can also measure the flexing, or bending of the orthotic. The electronic system, overall, will measure and record raw sensor data, pre-process it for external analysis and analyze the data. The sensors can also be used to measure gross foot/shoe movement to follow the gait cycle. Those skilled in the art will know how to determine the point in a gait cycle a person is in from the data provided by the sensors.

Operation

Figure 8:
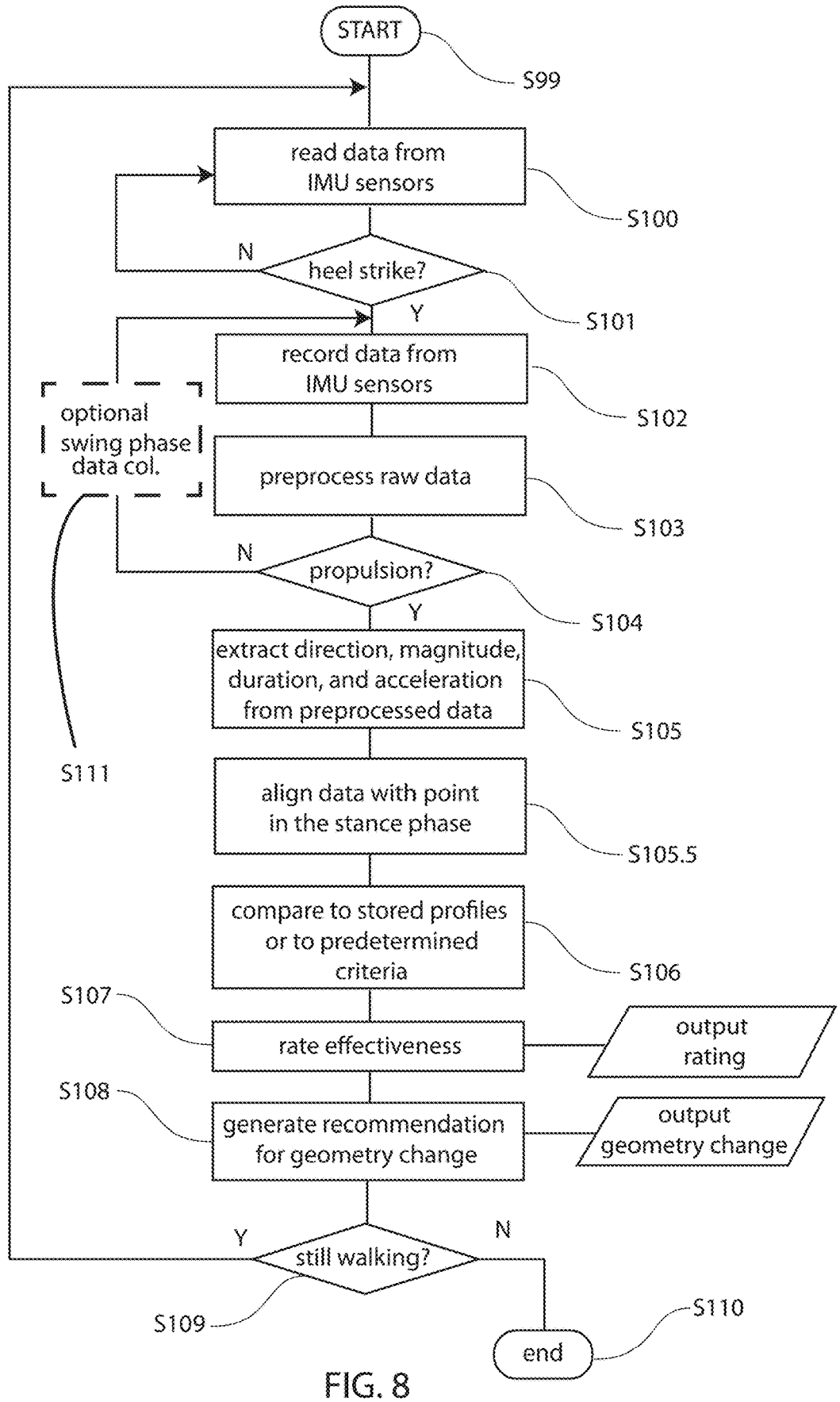
FIG. 8 is a flowchart of the major steps in the operation of an example instrumented orthotic.
Figure 9A:
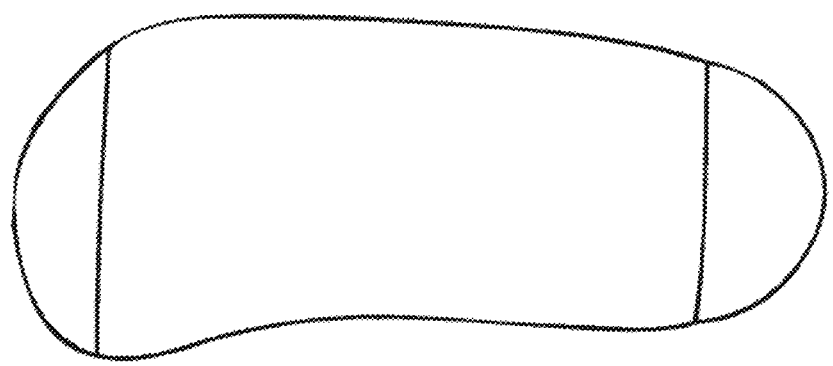
FIGS. 9a-9e show a variable orthotic from U.S. Pat. No. 8,490,301 viewed from multiple positions as an example of a variable foot orthotic.
Figure 9B:
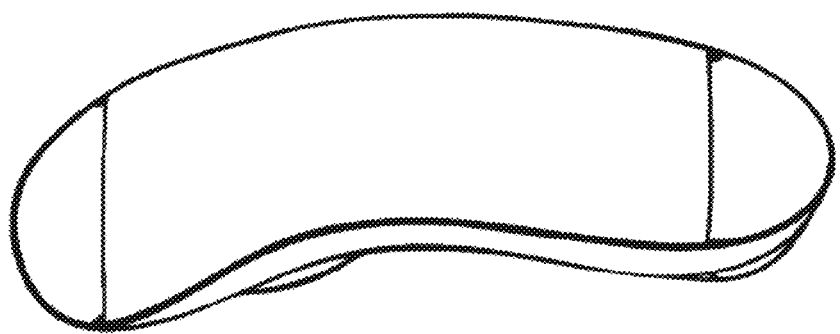
Figure 9C:
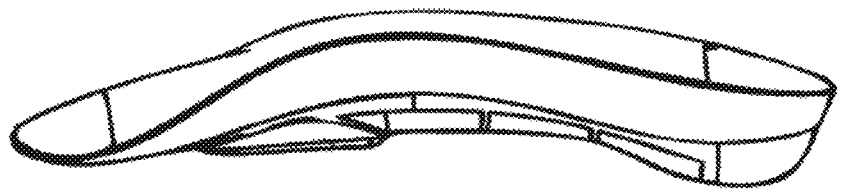
Figure 9D:
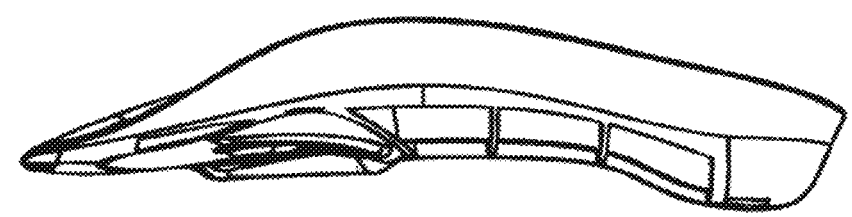
Figure 9E:
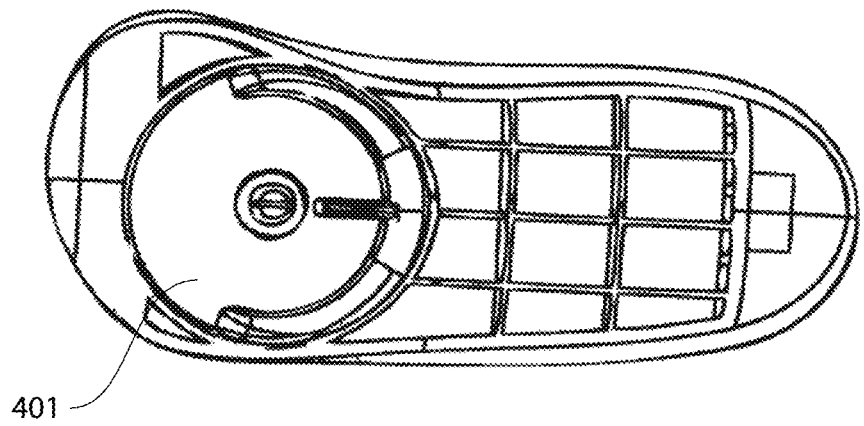

FIG. 8 shows a high level flow chart of the steps in an example operation of the described system embodiment. After starting S99, steps S100 and S101 implement a loop continuously reading data from the sensors to track the gait phase. When a heel strike is detected S101, the data is read and is recorded S102. A rapid spike in deceleration around the heel strike indicates the start of the stance phase. This occurs until toe-off is detected in step S104, ending the stance phase. After several steps, preprocessing is done that can organize and compress the data.

With the complete data for a stance phase, and optionally data from the swing phase, recorded, the operation extracts salient features of the data including flex, bend, or rotate direction, magnitude, timing, duration and the acceleration of flexing, bending, or rotating S105. The preprocessing and analysis in this embodiment includes taking the combination of raw data from the various sensors to create a normalized, coherent record of the motions and forces for each gait cycle.

In step S105.5 the relative timing point in the stance phase is aligned and associated with the movement data. The relative orthotic movement data can be aligned on a timeline with the stance phase of the gait cycle for analysis. A person may vary their speed even on a step-by-step basis; therefore the wall-clock time when a relevant data point is captured can be difficult to match for multiple steps from multiple persons. The more useful timing is the point in the gait cycle that a particular event occurs. Establishing a time normalized gait cycle permits comparison of multiple trials to each other.

In step S106 the salient data is compared to data from many trials with many users and many orthotic geometries to produce a rating of effectiveness S107. Data from trials with individuals with known foot problems and known optimum orthotics, including trials with alternant, non-optimum orthotics, are used for comparison. Comparisons to data previously taken from other subjects or the current subject with the same or other orthotics can be made to determine the effectiveness of the orthotic. Furthermore this data can be compared to data taken on bone and joint motion in a human performance lab. That data can be analyzed with neural nets or by classification and clustering techniques as taught in Seiner U.S. Pat. No. 8,139,822, Designation of a Characteristic of a Physical Capability by Motion Analysis Systems and Methods, to produce a rating of the effectiveness of an orthotic for a wearer. It can also be used to construct a predictive model for improved treatment.

The operation can optionally include step S108 and generate a recommendation for an improved orthotic for the tested user. By further analysis and comparison, S108 produces a recommendation to alter the geometry of the orthotic in an attempt to provide a better fit to a user and achieve an improved alignment. This improved alignment would help the user in achieving optimal clinical alignment of the lower extremity (reducing the rotational and vertical forces being transmitted up the kinetic chain of the lower extremity as a result of ground reaction forces). Recommendations to modify the geometry of the orthotic can include: suggesting a completely new orthotic or adding to or removing material on the present orthotic as traditionally done by podiatrists or orthotists. It could also include a setting change for a variable orthotic, or it could provide information to make a 3D printing of an optimized orthotic. If the user is still walking and still in the trial, the process repeats, starting back at S100.

The orthotic and the sole of the shoe have relative freedom of motion between them. As part of the analysis, the location of the ground can be determined by assuming it is a plane generally tangent to the earth and knowing the location of the shoe at a heel strike. To calculate realtive motion between the floor and the orthotic by effectively doing a 3D comparing of the location, motion and orientation of the shoe from the same information for one or more regions of the orthotic, shoe-orthotic relative motion can be determined.

Location of Computation Steps

Some of the steps of FIG. 8 are carried out by an instrumented orthotic, particularly by firmware and software executing on the embedded microprocessor 104. However, to keep the cost, size, and power dissipation low, many subsequent steps may be carried out by an application executing on a smart phone, tablet computer or other external computing device including a remote server 150. In that case, raw, preprocessed or partially analyzed data may be transmitted from the orthotic to a nearby computing and display device. In some embodiments data may be sent from the phone to a server and database via the cloud and the information returned from the server may supply the final information to have the phone display to a user.

The embodiment shown has a wireless transceiver for communicating with an external computing device such as a smart phone 105 or tablet computer or cloud-based server. After preliminary preprocessing under the control of software executing on the embedded microprocessor, the data is wirelessly sent to the external device for further processing and analysis. Steps S99 through S102 or alternatively S99 through S104 might be performed on the orthotics' electronics with the other steps performed on an external device or remote server and database. As mentioned, in some embodiments, the microprocessor may have sufficient computing power to perform more of, or all of, the steps of the analysis. If some data or all data is sent to a remote server with a database, the server may analyze the current data in light of other data from the same subject or in light of an aggregation of data including data from other subjects.

Variable Orthotics

The recommendation for an improved orthotic can include directing setting changes on a variable or adjustable orthotic. Teachings for adjustable orthotics include U.S. Pat. No. 8,749,115 Pas, et al.; U.S. Pat. No. 5,345,701 Smith; U.S. Pat. No. 8,490,301 Seiner; and U7707751 Avent, et al. FIGS. 9a-9e show views of an example variable orthotic from Seiner U.S. Pat. No. 8,490,301B2, Adjustable Forefoot Posting for Orthotic. Tilt settings on this device are changed by turning a selector wheel 401.

If an adjustable orthotic can have its setting changed electrically, the recommended change could be directly transmitted back to the orthotic to directly institute a geometry change. This might be practical if done when there is no weight on the post position.

With enough computing power embedded in an orthotic that can dynamically alter its geometry, the external electronic computing device may become optional. In some embodiments the external portable electronic device such as a smart cellphone, tablet, or special purpose unit can be used primarily to display results.

Variations

Variations can include versions that are connected by wires to a worn external computing device. The number of locations instrumented for measurement can vary. Sensors can include strain gauges and flex sensors, resistive, piezoelectric, and others. Another variation is a flexible printed circuit board with the electronic computers soldered onto it. The flexible circuit board could be permanently or temporarily adhered to any orthotic to transform it into an instrumented orthotic.

Alternate Embodiments

In some cases the relative position and movement between the sole of the shoe and the orthotic may be deemed to be a useful measurement, a wireless sensor could be imbedded into a shoe or temporary secured to either the inside or outside of the sole as depicted in FIGS. 1 and 6 as element 110. The sensors and computing within the orthotic could be used to instrument the shoe, or a much simpler, less power consuming electronics might be used.

Data could be transmitted directly to the external computing device or, saving power, may be sent to the orthotic directly above it. There are many suitable wireless technologies that can be used to achieve this including near field transmission.

These teachings can also be applied to other orthotic devices where there is independence of movement between the body and the orthotic. For example "An adjustable orthotic brace"—WO2003088865 Scorvo, describes a dynamically changing leg brace.

Previous work, including Aminian WO 2012/007855, provide enabling information including the use of inertial sensors attached to a shoe to measure foot position and orientation in 3D.

In some embodiments there may not be a local device doing significant computing but being used primarily as an output display device. In other embodiments there may not be a local computing device communicating with the instrumented orthotic. The instrumented orthotic may be transmitting to the Internet or other destination via cellular communications. WIFI or other technology. In other embodiments there may be no server connection necessary.

Other Uses for the System

The system can be used in research to collect data otherwise unavailable. Data collected by the dynamic orthotic can be compared to measurements taken in a human performance lab as a tool contributing to research in a predictive model that can help the clinician or consumer with a specific problem. This data could be used in an algorithm for the predictive model to assist clinicians and end users to better treat abnormalities, prevent injuries, as well as improve athletic performance. Algorithms can be constructed to more precisely identify individuals with correctable mechanically induced problems.

It is claimed:

1. An instrumented orthotic system comprising:
   a) an orthotic plate of a foot-conforming shape having at least a portion that is semi-flexible during movement or a gait cycle of a user, the orthotic plate configured to be removably inserted into a shoe of the user such that there is a freedom of motion between the orthotic plate and the shoe, the orthotic plate configured to temporarily bend under load to control, restrict, or reduce motion of a foot of the user during the movement or the gait cycle, the orthotic plate configured for complex flexing, bending, or rotating in sagittal, frontal, and transverse planes; and
   b) an electronic system embedded in the orthotic plate comprising:
      sensors in multiple locations on the orthotic plate configured to generate output signals conveying information related to a position, movement, and orientation of different regions in the semi-flexible portion; and
      a CPU and memory in electronic communication with the sensors where the memory comprises a program that reads sensor data in the output signals, and the CPU is configured to (1) pre-process the sensor data to determine a pattern of motion of the orthotic plate, the pattern of motion comprising a direction, magnitude, and timing, of flexing, bending, or rotating of the different regions of the orthotic plate at different points during the movement or the gait cycle of the user, and (2) compare the sensor data from a given sensor to data from other sensors on the orthotic plate, to previously taken data, and/or to motion of the shoe.

2. The instrumented orthotic system of claim 1, further comprising the other sensors on the orthotic plate, the other sensors on the orthotic plate configured to generate output signals conveying information related to a position, orientation and movement of a different distinct semi-flexible region of the orthotic plate, wherein the output signals from the other sensors on the orthotic plate facilitate a comparison between the timing, direction, or degree of flexing, bending, or rotating of the different distinct semi-flexible region of the orthotic plate to data from the given sensor, to previously taken data, and/or to motion of the shoe at the multiple points during the movement or the gait cycle of the user.

3. The instrumented orthotic system of claim 1, where the electronic system further comprises at least one sensor of the sensors configured to generate output signals conveying information related to ground reaction force.

4. The instrumented orthotic system of claim 1, further comprising an external computing unit, where the external computing unit has memory, and the memory comprises a program that analyses the pre-processed data transmitted from the electronic system and calculates the timing, the direction and a degree of flexing of the orthotic plate at multiple points in the gait cycle or during normal locomotion of the user.

5. The instrumented orthotic system of claim 1, further comprising an external computing unit where an external computing unit memory comprises a program that, based on the timing, the direction and a degree of flexing, bending, or rotating of the orthotic plate, rates an effectiveness of the orthotic plate for the user.

6. The instrumented orthotic system of claim 5, further comprising the external computing unit, where a rating of effectiveness includes a suggested change to geometry of the orthotic plate.

7. The instrumented orthotic system of claim 1, further comprising an external computing unit, wherein the external computing unit has memory, and the memory comprises a program that analyzes the pre-processed data transmitted from the electronic system and, based on the direction, magnitude, and timing, of flexing, bending, or rotating of the orthotic plate calculates motion of a subtalar and a midtarsal joint of the user at multiple points during the movement or in the gait cycle.

8. The instrumented orthotic system of claim 1, wherein the sensors include a three-axis accelerometer, a gyroscope, a magnetometer, and a strain gauge.

9. The instrumented orthotic system of claim 1, wherein a shape of the orthotic plate is adjustable.

10. The instrumented orthotic system of claim 1, wherein the electronic system is configured to measure x, y, and z components of position, acceleration, and velocity of the orthotic plate during the movement or the gait cycle of the user in response to forces generated by a foot and leg of the user on the orthotic plate.

11. A method of measuring effectiveness of an orthotic for a user wearing a shoe with the orthotic, the method comprising:
    in real-time, measuring, based on information in output signals from sensors embedded in multiple locations in the orthotic, with a CPU embedded in the orthotic, a position, speed, direction, and orientation of a location on the orthotic that flexes, bends, or rotates during a gait cycle during use, the orthotic configured to be removably inserted in the shoe of the user such that there is a freedom of motion between the orthotic and the shoe, the orthotic configured to temporarily bend under load to control, restrict, or reduce motion of a foot of the user during the gait cycle, the orthotic configured for complex flexing, bending, or rotating in sagittal, frontal, and transverse planes;
    determining a period of the gait cycle from sensor data;
    deducing a location of a plane of the ground from the sensor data;
    determining a pattern of motion of the orthotic, the pattern of motion comprising the direction, a magnitude, and a timing of flexing, bending, or rotating of different regions of the orthotic at different points in the gait cycle of the user; and
    determining relative motion between the orthotic and the ground.

12. The method of claim 11, further comprising normalizing a timing of the determined relative motion between the orthotic and the ground in terms of a percentage of a way through the gait cycle and analyzing the normalized timing to determine an effectiveness of the orthotic.

13. The method of claim 12, where the normalizing is at least partially accomplished by executing a program on an external computing device external to the orthotic.

14. The method of claim 12, where data related to the normalizing or the effectiveness is displayed to the user.

15. The method of claim 12, further comprising sending a command to the orthotic to change its geometry based upon the effectiveness, or manually changing the geometry of the orthotic based upon the effectiveness.

16. The method of claim 12, where analyzing normalized data is at least partially accomplished by executing a program on an external computing device or cloud based server.

17. The method of claim 12, further comprising sending data originating in the orthotic to a server.

18. The method of claim 12, further comprising an analysis of data originating in the orthotic being received from a server.

19. An instrumented orthotic system comprising:
   a) an orthotic plate with a foot-conforming shape having at least a portion of the orthotic plate that is semi-flexible during movement or a gait cycle of a user, the orthotic plate configured to be removably inserted into a shoe of the user such that there is a freedom of motion between the orthotic plate and the shoe, the orthotic plate configured to temporarily bend under load to control, restrict, or reduce motion of a foot of the user during the movement or the gait cycle, the orthotic plate configured for complex flexing, bending, or rotating in sagittal, frontal, and transverse planes; and
   b) an electronic system embedded in the orthotic plate comprising one or more processors and sensors in multiple locations on the orthotic, the sensors configured to generate output signals conveying information related to position, movement, and orientation of different regions in the semi-flexible portion of the orthotic plate;
      wherein the one or more processors are configured to (1) determine, based on the information in the output signals, a pattern of motion of the orthotic plate, the pattern of motion comprising a timing, direction, and degree of flexing, bending, or rotating of the different regions of the orthotic plate at multiple points during movement or the gait cycle of the user, and (2) compare sensor data from a given sensor to data from other sensors on the orthotic plate, to previously taken data, and/or to motion of the shoe.

20. The system of claim 19, wherein, the electronic system is configured to transmit, to an external computing unit, the timing, direction, and degree of flexing, bending, or rotating of the orthotic plate at the multiple points during the movement or the gait cycle of the user.

21. The system of claim 19, wherein the electronic system further comprises the other sensors on the orthotic plate, the other sensors on the orthotic plate configured to generate output signals conveying information related to a position, orientation, and movement of a different, distinct semi-flexible region of the orthotic plate,
   wherein the electronic system is configured such that the information in the output signals from the other sensors on the orthotic plate is indicative of a timing, direction, and degree of flexing, bending, or rotating of the different, distinct semi-flexible region of the orthotic plate at the multiple points in the gait cycle of the user, and
   facilitates a comparison between the timing, direction, and degree of flexing, bending, or rotating of the different distinct semi-flexible region of the orthotic plate to data from the sensors, to previously taken data, and/or to motion of the shoe at the multiple points during the movement of the user.

22. The system of claim 21, wherein an external computing unit is configured to perform the comparison between the timing, direction, and degree of flexing, bending, or rotating of the different distinct semi-flexible region of the orthotic plate and the data from the sensors, the previously taken data, and/or the motion of the shoe at the multiple points in the gait cycle of the user.

23. An instrumented orthotic evaluation system comprising one or more processors configured by machine-readable instructions to:
   a) receive output signals from an electronic system embedded in an orthotic plate worn by a user, the electronic system comprising sensors in multiple locations on the orthotic configured to generate the output signals, the output signals conveying information related to position, movement, and orientation of different regions of the orthotic plate, the orthotic plate having a foot-conforming shape and having at least a portion that is semi-flexible during movement or a gait cycle of the user, the orthotic plate configured to be removably inserted into a shoe of the user such that there is a freedom of motion between the orthotic plate and the shoe, the orthotic plate configured to temporarily bend under load to control, restrict, or reduce motion of a foot of the user during the movement or the gait cycle, the orthotic plate configured for complex flexing, bending, or rotating in sagittal, frontal, and transverse planes;
   b) determine, based on the information in the output signals, a pattern of motion of the orthotic plate, the pattern of motion comprising a timing, direction, and degree of flexing, bending, or rotating of the different regions of the orthotic plate at multiple points during movement or the gait cycle of the user; and
   c) compare sensor data from a given sensor to data from other sensors on the orthotic plate, to previously taken data, and/or to motion of the shoe.

24. The system of claim 23, wherein the electronic system further comprises the other sensors on the orthotic plate, the other sensors on the orthotic plate configured to generate output signals conveying information related to a position, orientation, and movement of a different, distinct semi-flexible region of the orthotic plate,
   wherein the one or more processors are further configured to:
      determine a timing, direction, and degree of flexing, bending, or rotating of the different, distinct semi-flexible region of the orthotic plate at the multiple points during the movement of the user, and
      compare the timing, direction, and degree of flexing, bending, or rotating of the different distinct semi-flexible region of the orthotic plate to data from the sensors, to previously taken data, and/or to motion of the shoe at the multiple points during the movement of the user.

25. The system of claim 23, wherein the one or more processors are included in one or more of a smart phone, a tablet computer, or a server.

26. A method for generating information about an orthotic worn by a user, the method comprising:
   a) forming an orthotic plate with a foot-conforming shape having at least a portion of the orthotic plate that is semi-flexible during movement or a gait cycle of a user of the orthotic plate, the orthotic plate configured to be removably inserted into a shoe of the user such that there is a freedom of motion between the orthotic plate and the shoe, the orthotic plate configured to temporarily bend under load to control, restrict, or reduce motion of a foot of the user during the movement or the gait cycle, the orthotic plate configured for complex flexing, bending, or rotating in sagittal, frontal, and transverse planes; and
   b) embedding an electronic system in the orthotic plate, the electronic system comprising sensors in multiple locations on the orthotic configured to generate output signals conveying information related to position, movement, and orientation of different semi-flexible regions of the orthotic plate;

wherein the electronic system is configured such that the information in the output signals is indicative of a timing, direction, and degree of flexing, bending, or rotating of the different regions of the orthotic plate at multiple points during movement or the gait cycle of the user; and wherein the electronic system is further configured to transmit the output signals to an external computing unit, the external computing unit configured to determine, based on the information in the output signals, a pattern of motion of the orthotic plate, the pattern of motion comprising the timing, direction, and degree of flexing, bending, or rotating of the different regions of the orthotic plate relative to data from other sensors on the orthotic plate, to previously taken data, and/or to motion of the shoe at multiple points during the movement or the gait cycle of the user.

27. The method of claim 26, further comprising providing the other sensors on the orthotic plate, the other sensors on the orthotic plate configured to generate output signals conveying information related to a position, orientation, and movement of a different, distinct semi-flexible region of the orthotic plate, wherein the electronic system is configured such that the information in the output signals from the other sensors on the orthotic plate is indicative of a timing, direction, and degree of flexing, bending, or rotating of the different, distinct semi-flexible region of the orthotic plate at the multiple points in the gait cycle of the user, and further wherein the electronic system is configured to transmit the output signals from the other sensors on the orthotic plate to the external computing unit to facilitate a comparison between the timing, direction, and degree of flexing, bending, or rotating of the different distinct semi-flexible region of the orthotic plate to data from the sensors, to previously taken data, and/or to motion of the shoe at the multiple points in the gait cycle of the user.

28. An instrumented orthotic system comprising:

a) an orthotic plate of a foot-conforming shape having at least a portion that is semi-flexible during movement or a gait cycle of a user, the orthotic plate configured to be removably inserted into a shoe of the user such that there is a freedom of motion between the orthotic plate and the shoe, the orthotic plate configured to temporarily bend under load to control, restrict, or reduce motion of a foot of the user during the gait cycle, the orthotic plate configured for complex flexing, bending, or rotating in sagittal, frontal, and transverse planes; and b) an electronic system embedded in the orthotic plate comprising:

sensors in multiple locations on the orthotic plate configured to generate output signals conveying information related to a position, movement, and orientation of different regions in the semi-flexible portion, wherein at least one sensor is located on a bottom of the orthotic plate;

a CPU and memory in electronic communication with the sensors where the memory comprises a program that reads sensor data in the output signals, and the CPU is configured to pre-process the sensor data to determine a direction, magnitude, and timing, of flexing, bending, or rotating of the different regions of the orthotic plate at different points during the movement or the gait cycle of the user such that the sensor data from a given sensor can be compared to data from other sensors on the orthotic plate, to previously taken data, and/or to motion of the shoe; determine bending of the orthotic plate in two dimensions based on the information in the sensor output signals; and determine ground reaction forces transmitted up a lower extremity of the user based at least on sensor data read from the bottom of the orthotic plate; and an external computing unit configured to receive the output signals from the sensors for storage in a database, wherein the external computing unit is configured to, based on stored output signals, determine an algorithm to facilitate a comparison between the timing, direction, and degree of flexing, bending, or rotating of the orthotic plate and corresponding pattern of movement information for other users, and predict motion for the other users;

wherein the database comprises the algorithm, the algorithm generating a classification model configured to predict how ground reaction forces would be transferred up a kinetic chain of the user.

* * * * *